(12) United States Patent
Vajdic

(10) Patent No.: US 11,969,251 B2
(45) Date of Patent: *Apr. 30, 2024

(54) APPARATUS FOR GENERATING AN ELECTROCARDIOGRAM

(71) Applicant: HeartBeam, Inc., Santa Clara, CA (US)

(72) Inventor: Branislav Vajdic, Los Gatos, CA (US)

(73) Assignee: HeartBeam, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/068,481

(22) Filed: Dec. 19, 2022

(65) Prior Publication Data

US 2023/0337959 A1 Oct. 26, 2023

Related U.S. Application Data

(63) Continuation of application No. 17/726,497, filed on Apr. 21, 2022, now Pat. No. 11,529,085.

(51) Int. Cl.
*A61B 5/322* (2021.01)
*A61B 5/00* (2006.01)
(Continued)

(52) U.S. Cl.
CPC ............ *A61B 5/332* (2021.01); *A61B 5/0006* (2013.01); *A61B 5/681* (2013.01); *A61B 5/6824* (2013.01);
(Continued)

(58) Field of Classification Search
CPC ...... G16H 40/67; A61B 5/332; A61B 5/0006; A61B 5/681; A61B 5/6824; A61B 5/6831; A61B 2560/0431
(Continued)

(56) References Cited

U.S. PATENT DOCUMENTS

| 4,216,780 A | 8/1980 | Rubel |
| 4,850,370 A | 7/1989 | Dower |

(Continued)

FOREIGN PATENT DOCUMENTS

| CN | 1668242 A | 9/2005 |
| CN | 101524272 A | 9/2009 |

(Continued)

OTHER PUBLICATIONS

Dower et al.; A clinical comparison of three vcg lead systems using resistance-combining networks; American Heart Journal; 55(4); pp. 523-534; Apr. 1958.

(Continued)

*Primary Examiner* — Carl H Layno
*Assistant Examiner* — Michael J Lau
(74) *Attorney, Agent, or Firm* — Shay Glenn LLP

(57) ABSTRACT

Wrist-wearable apparatuses that may be removed and used as a chest-applied cardiac device may include two chest electrodes on an inner surface of a strap (or strap regions), as well as two finger or more finger electrodes on the opposite side of the apparatus. The apparatus may be removed from the wrist and placed on a chest of a patient such that two electrodes are spaced at least five centimeters apart and in contact with the chest and held in place with two or more fingers to capture orthogonal cardiac signals that may be synthesized into a conventional 12-lead cardiac signal.

20 Claims, 8 Drawing Sheets

(51) Int. Cl.
   *A61B 5/332* (2021.01)
   *G16H 40/67* (2018.01)
(52) U.S. Cl.
   CPC ............ *A61B 5/6831* (2013.01); *A61B 5/746* (2013.01); *G16H 40/67* (2018.01); *A61B 2560/0431* (2013.01)
(58) Field of Classification Search
   USPC ........................................................ 600/508
   See application file for complete search history.

(56) References Cited

U.S. PATENT DOCUMENTS

| | | | |
|---|---|---|---|
| 5,630,664 | A | 5/1997 | Farrelly |
| 5,724,580 | A | 3/1998 | Levin et al. |
| 6,047,203 | A | 4/2000 | Sackner et al. |
| 6,052,615 | A | 4/2000 | Feild et al. |
| 6,363,274 | B1 | 3/2002 | Scalisi et al. |
| 6,507,753 | B1 | 1/2003 | Xue et al. |
| 6,607,480 | B1 | 8/2003 | Bousseljot et al. |
| 6,625,483 | B2 | 9/2003 | Hoium et al. |
| 7,266,408 | B2 | 9/2007 | Bojovic et al. |
| 7,477,935 | B2 | 1/2009 | Palreddy et al. |
| 7,647,093 | B2 | 1/2010 | Bojovic et al. |
| 7,801,591 | B1 | 9/2010 | Shusterman |
| 8,209,002 | B2 | 6/2012 | Vajdic et al. |
| 8,369,936 | B2 | 2/2013 | Farringdon et al. |
| 8,615,290 | B2 | 12/2013 | Lin et al. |
| 8,676,304 | B2 | 3/2014 | Fischell et al. |
| 8,700,137 | B2 | 4/2014 | Albert |
| 8,781,566 | B2 | 7/2014 | John et al. |
| 8,818,482 | B2 | 8/2014 | Phillips et al. |
| 9,364,158 | B2 | 6/2016 | Banet et al. |
| 10,117,592 | B2 | 11/2018 | Bojovic et al. |
| 10,433,744 | B2 | 10/2019 | Bojovic et al. |
| 10,729,347 | B1* | 8/2020 | Schleicher ............. A61B 5/332 |
| 11,071,490 | B1 | 7/2021 | Vajdic et al. |
| 11,419,538 | B2 | 8/2022 | Vajdic et al. |
| 11,445,963 | B1 | 9/2022 | Belicev et al. |
| 11,529,085 | B1 | 12/2022 | Vajdic |
| 2002/0045836 | A1 | 4/2002 | Alkawwas |
| 2003/0032871 | A1 | 2/2003 | Selker et al. |
| 2003/0083586 | A1 | 5/2003 | Ferek-Petric |
| 2003/0083587 | A1 | 5/2003 | Ferek-Petric |
| 2004/0087864 | A1 | 5/2004 | Grouse |
| 2004/0138574 | A1 | 7/2004 | Groenewegen et al. |
| 2005/0027203 | A1 | 2/2005 | Umeda et al. |
| 2005/0215918 | A1 | 9/2005 | Frantz et al. |
| 2005/0234354 | A1 | 10/2005 | Rowlandson et al. |
| 2006/0009698 | A1 | 1/2006 | Banet et al. |
| 2006/0030782 | A1 | 2/2006 | Shennib |
| 2006/0224072 | A1 | 10/2006 | Shennib |
| 2007/0021677 | A1 | 1/2007 | Markel |
| 2008/0027330 | A1 | 1/2008 | Naghavi et al. |
| 2008/0113650 | A1 | 5/2008 | Engstrom |
| 2008/0161715 | A1 | 7/2008 | Stivoric et al. |
| 2009/0112105 | A1 | 4/2009 | Clayman |
| 2009/0281421 | A1 | 11/2009 | Culp et al. |
| 2009/0281440 | A1 | 11/2009 | Farazi et al. |
| 2009/0299206 | A1 | 12/2009 | Wang et al. |
| 2010/0017420 | A1 | 1/2010 | Archer et al. |
| 2010/0023081 | A1 | 1/2010 | Audet et al. |
| 2010/0076331 | A1 | 3/2010 | Chan et al. |
| 2010/0130845 | A1 | 5/2010 | Clayman |
| 2010/0174204 | A1 | 7/2010 | Danteny |
| 2010/0240980 | A1 | 9/2010 | Zhu et al. |
| 2011/0015496 | A1 | 1/2011 | Sherman et al. |
| 2011/0105928 | A1 | 5/2011 | Bojovic et al. |
| 2011/0224565 | A1 | 9/2011 | Ong et al. |
| 2011/0301435 | A1 | 12/2011 | Albert et al. |
| 2011/0306859 | A1 | 12/2011 | Saldivar et al. |
| 2012/0022385 | A1 | 1/2012 | Shimuta et al. |
| 2012/0059271 | A1 | 3/2012 | Amital et al. |
| 2012/0116176 | A1 | 5/2012 | Moravec et al. |
| 2012/0116240 | A1 | 5/2012 | Chou |
| 2012/0136266 | A1 | 5/2012 | Grady |
| 2012/0184858 | A1 | 7/2012 | Harlev et al. |
| 2012/0283586 | A1 | 11/2012 | Song et al. |
| 2013/0125906 | A1 | 5/2013 | Hon |
| 2013/0172723 | A1 | 7/2013 | Baxi et al. |
| 2013/0331665 | A1 | 12/2013 | Libbus et al. |
| 2014/0114166 | A1 | 4/2014 | Baxi |
| 2014/0155723 | A1 | 6/2014 | Levin et al. |
| 2014/0163349 | A1 | 6/2014 | Amital et al. |
| 2014/0257122 | A1 | 9/2014 | Ong et al. |
| 2015/0018660 | A1 | 1/2015 | Thomson et al. |
| 2015/0057512 | A1 | 2/2015 | Kapoor |
| 2016/0015286 | A1 | 1/2016 | Gitlin et al. |
| 2016/0022162 | A1 | 1/2016 | Ong et al. |
| 2016/0045166 | A1 | 2/2016 | Gheeraert et al. |
| 2016/0135706 | A1 | 5/2016 | Sullivan et al. |
| 2016/0188823 | A1 | 6/2016 | Rowlandson et al. |
| 2016/0287172 | A1* | 10/2016 | Morris ................. A61B 5/7264 |
| 2017/0127966 | A1 | 5/2017 | Wu et al. |
| 2017/0188861 | A1 | 7/2017 | Schreck et al. |
| 2018/0004904 | A1 | 1/2018 | Phillips |
| 2018/0064356 | A1 | 3/2018 | Mendenhall et al. |
| 2019/0069789 | A1 | 3/2019 | Bojovic et al. |
| 2019/0117100 | A1* | 4/2019 | Rollie .................. A61B 5/0006 |
| 2019/0298200 | A1* | 10/2019 | Wiesel ............... A61B 5/02416 |
| 2019/0336020 | A1* | 11/2019 | Kranz ..................... A61B 5/318 |
| 2020/0113454 | A1 | 4/2020 | Wu et al. |
| 2020/0315480 | A1* | 10/2020 | Hwang .................. A61B 5/316 |
| 2020/0375493 | A1 | 12/2020 | Kranz |
| 2021/0113136 | A1 | 4/2021 | Bojovic et al. |
| 2021/0169392 | A1 | 6/2021 | Albert et al. |
| 2021/0267525 | A1 | 9/2021 | Albert |
| 2022/0015679 | A1 | 1/2022 | Shvilkin et al. |
| 2022/0015680 | A1 | 1/2022 | Vajdic et al. |
| 2022/0061759 | A1 | 3/2022 | Galeev et al. |
| 2022/0211287 | A1 | 7/2022 | Vajdic et al. |

FOREIGN PATENT DOCUMENTS

| | | |
|---|---|---|
| CN | 202854760 U | 4/2013 |
| CN | 203000927 U | 6/2013 |
| EP | 1227752 A1 | 8/2002 |
| EP | 0944353 B1 | 11/2002 |
| EP | 1659936 A1 | 3/2005 |
| JP | H0391304 U | 9/1991 |
| JP | 2007195690 A | 8/2007 |
| WO | WO01/70105 A2 | 9/2001 |
| WO | WO2015/177594 A2 | 11/2015 |
| WO | WO2017/208040 A2 | 12/2017 |
| WO | WO2020/0232040 A1 | 11/2020 |
| WO | WO2022/104160 A1 | 5/2022 |
| WO | WO2022/147520 A1 | 7/2022 |
| WO | WO2023/060119 A1 | 4/2023 |

OTHER PUBLICATIONS

Goff et al.; 2013 ACC/AHA guideline on the assessment of cardiovascular risk: a report of the American College of Cardiology/American Heart Association Task Force on Practice Guidelines; Journal of the American College of Cardiology; 63(25 Part B); pp. 2935-2959; Jul. 1, 2014.

Goff et al.; 2013 ACC/AHA guideline on the assessment of cardiovascular risk: a report of the American College of Cardiology/American Heart Association Task Force on Practice Guidelines; Journal of the American College of Cardiology;; 129(25 Suppl 2); pp. S49-S73; Jun. 2014.

Kligfield et al.; Recommendations for the standardization and interpretation of the electrocardiogram: Part I: The Electrocardiogram and Its Technology A Scientific Statement From the American Heart Association Electrocardiography and Arrhythmias Committee, Council on Clinical Cardiology; the American College of Cardiology Foundation: and the Heart Rhythm Society Endorsed by the International Society for Computerized Electrocardiology; 49(10); pp. 1109-1127, Mar. 13, 2007.

Marma et al.; Systematic examination of the updated Framingham heart study general cardiovascular risk profile; Circulation; 120(5): p. 384; Aug. 1, 2009.

(56) References Cited

OTHER PUBLICATIONS

Med-Tech Innovation; The ECG device the of a credit card; Aug. 23, 2017; retrieved from the internet (https://www.med-technews.com/news/the-ecg-device-the-size-of-a-credit-card/) on Jan. 26, 2021.

Perk et al.; European Guidelines on cardiovascular disease prevention in clinical practice (version 2012) The Fifth Joint Task Force of the European Society of Cardiology and Other Societies on Cardiovascular Disease Prevention in Clinical Practice; European heart Journal; 33(13); pp. 1635-1701; Jul. 1, 2012.

Rakshit et al.; EKF with PSO technique for delineation of P and T wave in electrocardiogram (ECG) signal; In 2015 2nd International Conference on Signal Processing and Integrated Networks (SPIN); IEEE; pp. 696-701; Feb. 19, 2015.

Sun et al.; Characteristic wave detection in ECG signal using morphological transform; BMC cardiovascular disorders; 5(1); pp. 1-7; Dec. 2005.

Belicev et al.; U.S. Appl. No. 17/948,099 entitled "Method and apparatus for reconstructing electrocardiogram (ECG) data," filed Sep. 19, 2022.

Vajdic et al.; U.S. Appl. No. 18/260,318 entitled "Anbulatory electrocardiogram patch devices and methods," filed Jul. 3, 2023.

Vajdic et al.; U.S. Appl. No. 18/252,803 entitled "Compact mobile three-lead cardiac monitoring device with hybrid electrode," filed May 12, 2023.

Shvilkin et al.; U.S. Appl. No. 18/324,111 entitled "Hand held device for automatic cardiac risk and diagnostic assessment," filed May 25, 2023.

* cited by examiner

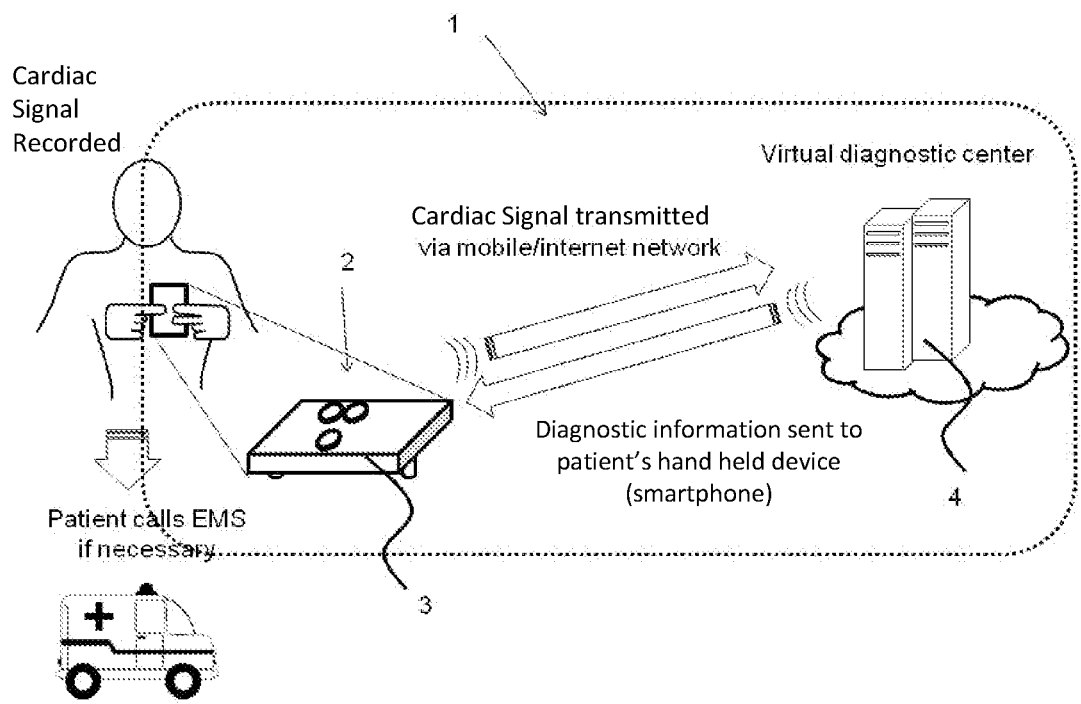
FIG. 1B
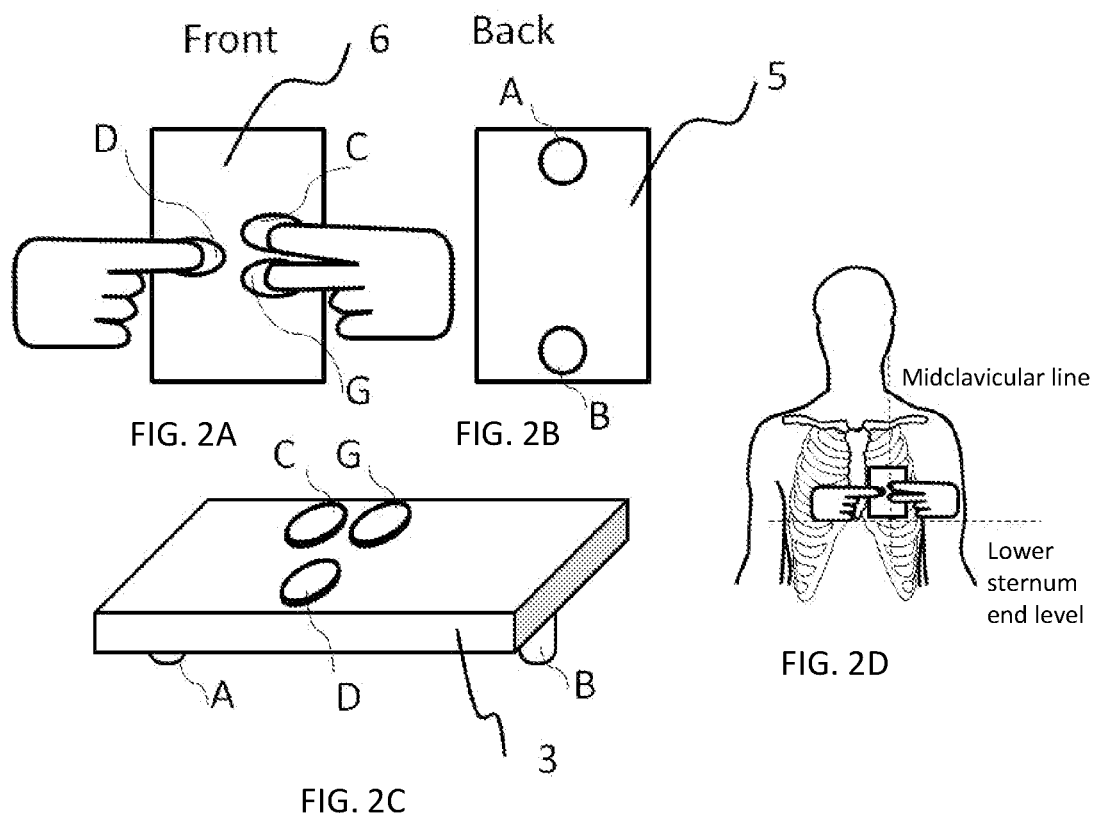
FIG. 2A  FIG. 2B
FIG. 2C
FIG. 2D

APPARATUS FOR GENERATING AN ELECTROCARDIOGRAM

CLAIM OF PRIORITY

This application is a continuation of U.S. patent application Ser. No. 17/726,497, filed Apr. 21, 2022, titled "APPARATUS FOR GENERATING AN ELECTROCARDIOGRAM," now U.S. Pat. No. 11,529,085, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Handheld electrocardiogram (ECG) devices may be used by a patient (or a medical professional) to capture and record ECG data. Unfortunately, despite the potential benefit to such hand-held apparatuses, none have found widespread use. This may be due in part, to the size, weight and ease of use, as well as the need to carry and apply the apparatus during the day, which may be inconvenient, and disruptive. Although devices that may be worn continuously that may track ECG have also been proposed, these devices may be uncomfortable and/or may have a low accuracy, particularly if measuring device from regions other than the chest.

Therefore, there is a need for a compact ECG device that is capable of capturing cardiac signals from the chest that are easy to use, convenient and still highly accurate.

SUMMARY OF THE DISCLOSURE

The methods and apparatuses (e.g., systems, devices, etc.) described herein may relate generally to electrocardiography.

In general, described herein are methods and apparatuses for recording and analyzing cardiac signals from a patient using a wrist worn ECG 'watch' device (or more generally, a w wrist-worn device) that may be taken off of the wrist and held against the subject's chest by the subject. The apparatus is configured so that, when removed from the subject's wrist, it may assume a configuration that may be easily and accurately placed against the chest and held by the subject to provide three orthogonal leads that may be used to generate a synthetic 12 lead ECG signal that comports with traditional 12-lead ECG signals and may be easily read by those trained in standard electrocardiograms.

These apparatuses may typically include a strap (which in some examples has multiple strap regions) that and a housing (including a display). When not used to record ECG signals on the subject's chest, the apparatus may be a wrist-worn device that may display the time and/or other information (e.g., heart rate/pulse, blood oxygenation, steps/movement, etc.). In some examples the apparatus may be configured as a smartwatch (e.g., phone, etc.) or any other wrist-worn device. The apparatus may include a first configuration that is configured as a wrist-worn strap that may be secured to the subject's wrist. At least two electrodes may be on the inner surface (of the strap and/or housing) and at least two electrodes may be positioned on an outer surface (e.g., on the strap and/or housing). The inner electrodes are configured so that when the apparatus is removed from the wrist, and transitioned to a linear configuration the inner electrodes may be separated from each other by a predefined distance, e.g., of greater than 5 cm (greater than 6 cm, greater than 7 cm, greater than 8 cm, greater than 9 cm, greater than 10 cm, greater than 11 cm, etc.), e.g., between 6 and 14 cm (e.g., between 6 and 13 cm, between 6 and 12 cm, between 6 and 11 cm, between 8 and 10 cm, etc.). The inner (chest) electrodes may provide cardiac lead signals in combination with the outer (hand/finger) electrodes and may provide a set of orthogonal three-lead cardiac signals.

As used herein, a cardiac signal may refer to a voltage produced by a human heart as sensed between selected points on the surface of a subject's body and may also be referred to as cardiac electrical signals (e.g., electrocardiac signals). These cardiac signals may include electrocardiogram (ECG) signals. It should be understood that although the term ECG (electrocardiogram) is commonly used to refer to conventional 12-lead ECG signals, the cardiac signals (cardiac electrical signals) described herein are not limited to these conventional 12-lead ECG signals.

Described herein are mobile, hand-held devices for capturing cardiac signals. The device may include a first electrode on an inner surface of a first wrist band region, and a second electrode on an inner surface of a second wrist band region (or in some examples a housing). The second wrist band region may be on a separate wrist band, or it may be a second region of the same wrist band as the first wrist band region. The third and fourth electrodes are configured to be contacted by a finger of a first and second hand, respectively, when the apparatus is held by the subject against the subject's chest. In some cases the subject, which may be a patient or user, may hold the unbuckled/unfastened apparatus after removing it from the wrist, in a linear configuration against the subject's chest.

In some examples the apparatus includes a first wrist band region that is part of a first wrist band that is configured to removably couple to a second wrist band region that is part of a second wrist band. The device may also include a housing coupled to the first wrist band and the second wrist band, where the first wrist band, the second wrist band, and the housing are configured to form a continuous loop to be worn on a wrist. The housing may include electrical circuits configured to receive electrical signals from the first, second, third, and fourth electrodes, and determine a set of three-lead cardiac signals from the electrical signals, wherein the set of three-lead cardiac signals include sufficient information to synthesize (e.g., determine, derive) conventional 12-lead electrocardiogram (ECG) information. The housing may also include a processor and/or other circuitry as descried herein for recording and/or analyzing an ECG signal. The housing may also include circuitry for a clock/watch that may be shown on a display. The same processor and circuitry may be used and/or integrated with the circuitry for measuring, analyzing, storing and transmitting the ECG signals as described herein (including the 3 orthogonal leads).

Any of the devices may include a first electrode and a second electrode configured to contact a patient's chest. Furthermore, in any of the devices described herein the first electrode and the second electrode may be configured to be separated by a distance of at least five centimeters when the first electrode and the second electrode are receiving electrical signals from a patient's heart.

In any of the devices described herein, a third electrode may be configured to be placed in contact with a finger from a first hand and the fourth electrode may be configured to be placed in contact with a finger from a second hand, the second hand being different than the first hand. Furthermore, in any of the devices described herein, the electrical circuits may be further configured to record one or more sets of three-lead cardiac signals.

In the devices described herein, the apparatus, including in some cases the electrical circuits within the housing, may be further configured to generate conventional 12-lead ECG information from at least one set of three-lead cardiac signals. Alternatively, in some examples the apparatus may be configured so that an external or remote processor is used to generate conventional 12-lead ECG information from the recorded signals (e.g., forming 3 orthogonal leads). Furthermore, in the apparatuses (e.g., devices, systems, etc. including wrist-worn devices and/or watches) described herein, the apparatus may include a housing further comprises a display configured to display instructions to capture one or more sets of three-lead cardiac signals with the device. The display may be configured to display the time or other information during operation of the apparatus as a watch when worn encircling the wrist. In some examples the housing may include a display configured to display instructions to capture one or more sets of three-lead cardiac signals with the device. In some examples, the housing may additionally or alternatively include a speaker configured to provide audible instructions to capture one or more sets of three-lead cardiac signals with the device.

In any of the apparatuses described herein, the device may include a transmitter configured to transmit one or more sets of three-lead cardiac signals to a second device. Furthermore, the first wrist band may include conductors to electrically couple the first electrode and the second electrode to the electrical circuits and the second wrist band may include conductors to electrical couple the third electrode and the fourth electrode to the electrical circuits.

In some examples a wearable cardiac diagnosis device is described. The wearable cardiac diagnosis device may comprise a first wrist band region including a first electrode, a second wrist band region including a second electrode, and a third and a fourth electrode on an outer surface of the apparatus, and the apparatus is configured to removably couple to the first wrist band region to the second wrist band region and to form a continuous band to be worn on a subject's wrist. The apparatus may include a housing may that be coupled to the first wrist band region and the second wrist band region and may include a display, and in some examples electrical circuits configured to operate in a first mode to display time of day information on the display and operate in a second mode to receive electrical signals from the first, second, third, and fourth electrodes, and determine a set of three-lead cardiac signals from the electrical signals.

In any of the wearable apparatuses described herein, the set of three-lead cardiac signals may include sufficient information to synthesize conventional 12-lead electrocardiogram (ECG) information. In some examples, the first electrode and the second electrode may be configured to be separated by at least 5 centimeters and simultaneously contact a chest of a patient. In some examples, the third electrode may be configured to receive a first cardiac signal from a finger of a first hand and the fourth electrode may be configured to receive a second cardiac signal from a finger of a second hand different from the first hand.

In any of the wearable apparatuses described herein, the housing may further enclose a wireless transmitter configured to transmit three-lead cardiac data when the wearable cardiac diagnosis device is operating in the second mode. In some examples, the apparatuses may be configured to display instructions to capture one or more sets of three-lead cardiac signals when the wearable cardiac diagnosis device is operating in the second mode.

In any of the apparatuses described herein, the apparatus may be configured to display information regarding electrode placement when the wearable device is operating in the second mode. The housing may further enclose a speaker configured to provide audible instructions to capture one or more sets of three-lead cardiac signals when the wearable cardiac diagnosis device is operating in the second mode.

This patent application may be related to U.S. patent application Ser. No. 17/092,152, titled "MOBILE THREE-LEAD CARDIAC MONITORING DEVICE AND METHOD FOR AUTOMATED DIAGNOSTICS," filed on Nov. 6, 2020, and U.S. patent application Ser. No. 17/443,456, titled "ELECTROCARDIOGRAM PATCH DEVICES AND METHODS," filed on Jul. 26, 2021, and U.S. patent application Ser. No. 17/570,368, titled "ELECTROCARDIOGRAM PATCH DEVICES AND METHODS," filed on Jan. 6, 2022, each of which is herein incorporated by reference in its entirety.

For example, described herein are wrist-worn apparatuses configured to measure 12-lead ECG signals, apparatus comprising: a first wrist band portion including a first electrode on an inner side of the first wrist band portion and a third electrode on an opposite side of the first wrist band portion; a second wrist band portion including a second electrode on an inner side of the second wrist band portion and a fourth electrode on an opposite side of the second wrist band portion, wherein the first wrist band portion and second wrist band are configured to form a continuous loop worn on a subject's wrist, and are further configured to be spread apart and positioned on the subject's chest so that the first electrode and the second electrode are separate by between 6 and 14 cm to measure bioelectric signals from the subject's chest, wherein the third electrode is configured to measure bioelectric signals from the subject's right hand and the fourth electrode is configured to measure bioelectric signals from the subject's left hand; a resistive network forming a central point in a sagittal plane through the subject's chest passing between the third and fourth electrodes when the first wrist band portion and the second wrist band portion are held against the subject's chest, wherein three orthogonal cardiac leads are formed from the first, second, third and fourth electrodes and the central point; and a processor configured to process the three orthogonal cardiac leads derived from the first, second, third and fourth electrodes.

The third electrode may be configured to be placed in contact with a finger from the subject's first hand and the fourth electrode is configured to be placed in contact with a finger from the subject's second hand, the subject's second hand being different than the subject's first hand.

The processor may be configured to record and transmit the three orthogonal cardiac leads. The processor may be configured to synthesize conventional 12-lead electrocardiogram (ECG) information from the three orthogonal leads. The processor may be housed within a housing positioned between the first wrist band portion and the second wrist band portion.

As mentioned, any of these apparatuses may include a housing enclosing the resistive network and processor, wherein the housing is positioned between the first wrist band portion and the second wrist band portion.

Any of these apparatuses may include a display configured to display a time output when the first wrist band portion and the second wrist band form a continuous loop worn on a subject's wrist. The display may be configured to indicate an orientation of the apparatus when held against the subject's chest. Any of these apparatuses may include a clasp configured to secure the first wrist band portion to the second wrist band portion around the subject's wrist.

The apparatus may include a wireless transmitter configured to transmit data from the three orthogonal cardiac leads.

The processor may be configured to output instructions to capture one or more sets of three-lead cardiac signals when the first wrist band portion and second wrist band are spread apart.

For example, a wrist-worn apparatus configured to measure 12-lead ECG signals may include: a first wrist band portion including a first electrode on an inner side of the first wrist band portion and a third electrode on an opposite side of the first wrist band portion; a second wrist band portion including a second electrode on an inner side of the second wrist band portion and a fourth electrode on an opposite side of the second wrist band portion, wherein the first wrist band portion and second wrist band are configured to form a continuous loop worn on a subject's wrist, and are further configured to be spread apart and positioned on the subject's chest so that the first electrode and the second electrode are separate by between 6 and 14 cm to measure bioelectric signals from the subject's chest, wherein the third electrode is configured to measure bioelectric signals from the subject's right hand and the fourth electrode is configured to measure bioelectric signals from the subject's left hand; a housing coupled between the first wrist band portion and the second wrist band portion comprising a display face; a resistive network with the housing and forming a central point in a sagittal plane through the subject's chest passing between the third and fourth electrodes when the first wrist band portion and the second wrist band portion are held against the subject's chest, wherein three orthogonal cardiac leads are formed from the first, second, third and fourth electrodes and the central point; and a processor configured to process the three orthogonal cardiac leads derived from the first, second, third and fourth electrodes and to synthesize conventional 12-lead electrocardiogram (ECG) information from the three orthogonal cardiac leads.

Also described herein are methods of detecting a cardiac signal from a subject, the method comprising: removing a wrist-worn apparatus from the subject's wrist; placing a first wrist band portion of the wrist-worn apparatus against the subject's chest so that a first electrode on an inner surface of the first wrist band portion is in contact with the subject's chest and a second electrode on an inner surface of a second wrist band portion against is in contact with the subject's chest, wherein the first electrode is separated from the second electrode by between about 6 cm and 12 cm; placing a finger of a first hand against a third electrode on an outer surface of the wrist-worn apparatus and an finger of a second hand against a fourth electrode of the wrist-worn apparatus; and measuring three orthogonal leads using a resistive network forming a central point in a sagittal plane through the subject's chest passing between the third and fourth electrodes when the first wrist band portion and the second wrist band portion are held against the subject's chest, wherein three orthogonal cardiac leads are formed from the first, second, third and fourth electrodes and the central point; processing the three orthogonal cardiac leads to synthesize conventional 12-lead electrocardiogram (ECG) information; and outputting the conventional 12-lead ECG information.

Any of these methods may include removing the wrist-worn apparatus from the subject's wrist by uncoupling a latch on the wrist-worn apparatus. Any of these methods may include transmitting the three orthogonal cardiac leads from the wrist-worn apparatus to a remote processor to process the three orthogonal leads.

Placing the finger of the first hand against the third electrode may comprise placing the finger of the first hand against the third electrode on an outer surface of the first wrist band portion and placing the finger of the second hand against the fourth electrode comprises placing the finger of the second hand against the fourth electrode on an outer surface of the second wrist band portion. In some examples placing the finger of the first hand against the third electrode comprises placing the finger of the first hand against a housing comprising a display, wherein the housing is between the first wrist band portion and the second wrist band portion.

Processing the three orthogonal leads may comprise processing the using a processor housed within a housing positioned between the first wrist band portion and the second wrist band portion. Any of these methods may include display a time output on a display of the wrist-worn apparatus when the wrist-worn apparatus is worn on the subject's wrist.

The methods described herein may include instructing the subject, via an output from the wrist-worn apparatus, how to hold the wrist-worn apparatus against the subject's chest.

Any of the methods and apparatuses described herein may be configured to monitor the patient's cardiac activity while wearing the apparatus on the wrist, and may alert the wearer (or a caregiver) to take a chest recording with the apparatus if the apparatus detects activity that exceeds a monitoring threshold. For example, any of these apparatuses may include one or more sensor, e.g., electrodes, optical sensors (e.g., Photoplethysmography or PPG sensors), etc., and may include software, hardware or firmware, e.g., as part of a controller, to monitor the output of the sensor periodically (e.g., about every x minutes, where x is 0.1, 0.2, 0.25, 0.3, 0.5, 1, 2, 3, 4, 5, 10, 15, 20, 25, 30, 35, 40, 45, 60, etc.) or continuously to determine if the sensed signal falls within a range or has a pattern characteristic of a cardiac problem. The apparatus may make an alert on the wrist-worn apparatus, by one or more of: displaying a message (text, graphic, etc.), flashing a light, emitting a tone, etc. In some examples the apparatus may send a message (e.g., SMS message/text message, email, etc.) to the wearer and/or caregiver. In some examples the message may include a recommendation or instructions that a "chest recording is advised". Thus, any of these apparatuses may include a monitoring mode when the apparatus is worn on the wrist. The apparatus may be configured to enter the monitoring mode manually or automatically, such as when the apparatus senses that the device is being worn on the wrist by a user.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative examples, and the accompanying drawings of which:

FIG. 1B shows a view of another example of a system for cardiac signal detection.

FIGS. 2A, 2B and 2C show front, back and axonometric views, respectively, of an example of a handheld device.

FIG. 2D shows a front view of a device placed against the patient's body in a recording position.

Figure 3A:
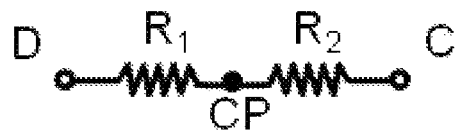

The example in FIG. 3A shows a simple electrical scheme for obtaining a central point (CP) signal by connecting the electrodes of both hands via a simple resistive network consisting of two resistors.

Figure 3B:
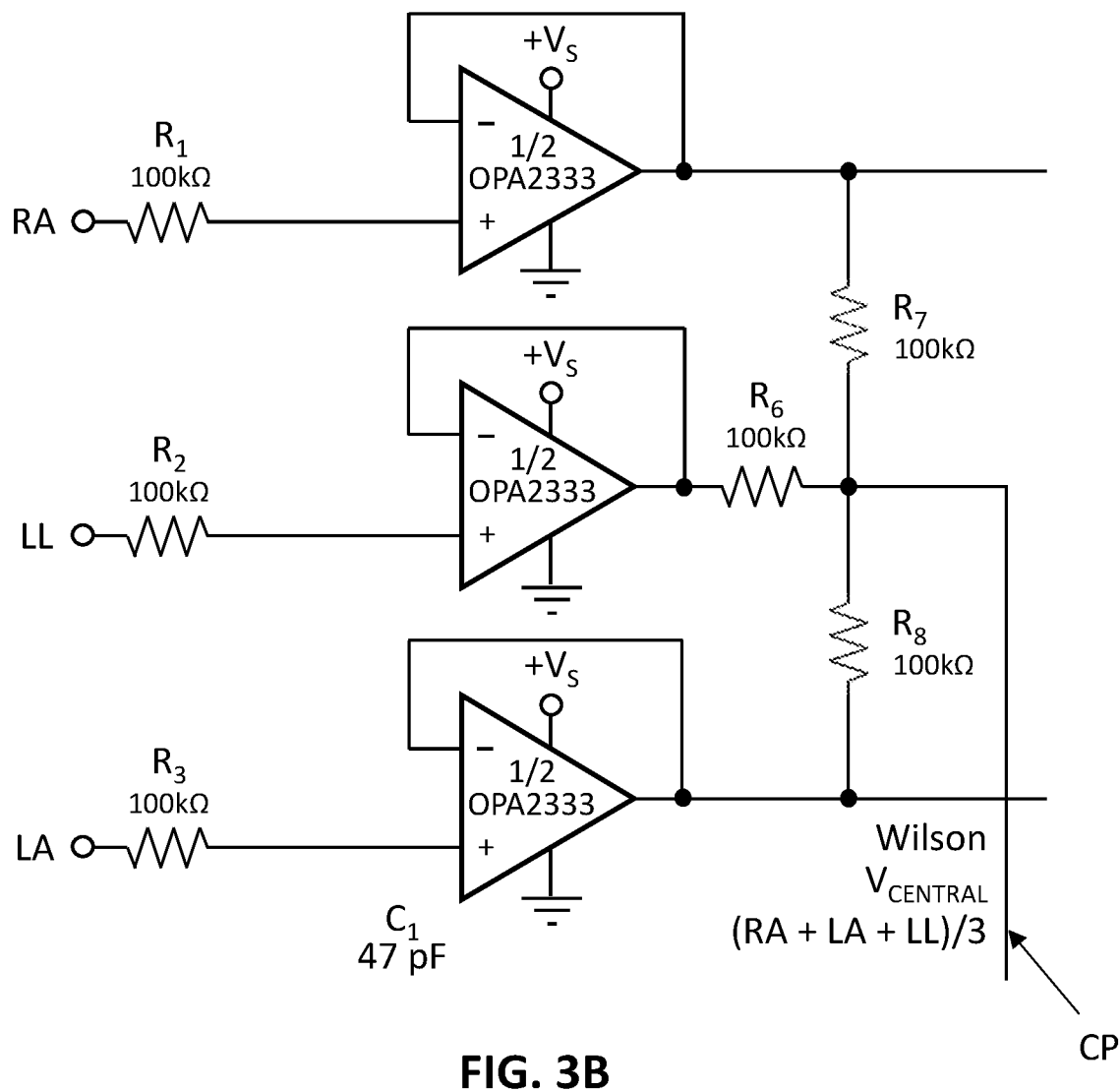

FIG. 3B shows an electrical scheme for obtaining the CP signal using buffering and averaging via operational amplifiers.

Figures 4A, 4B:
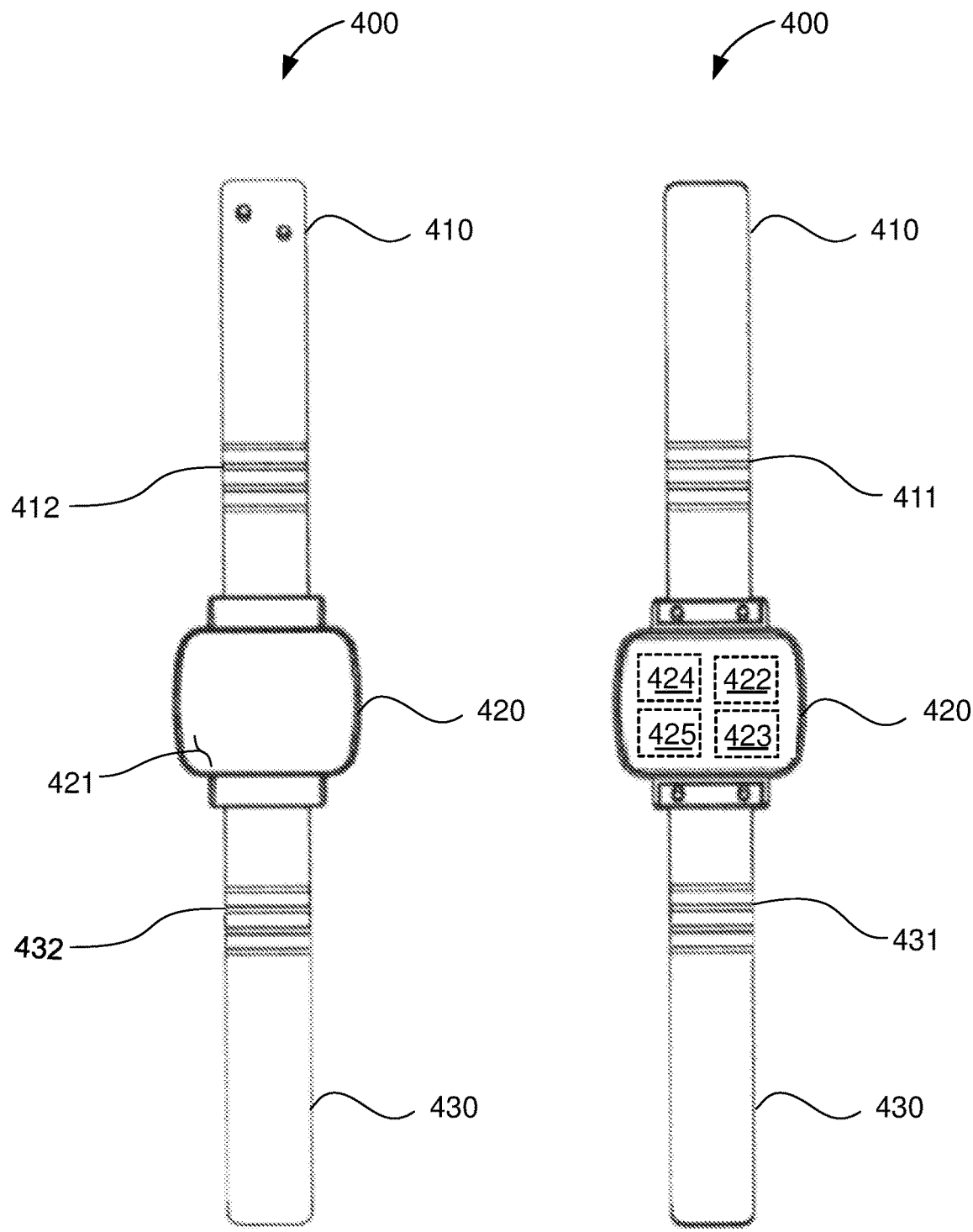

FIG. 4A shows a front view of an example of a wrist-worn apparatus as described herein.

FIG. 4B shows a rear view of the wrist-worn apparatus of FIG. 4A.

Figure 5A:
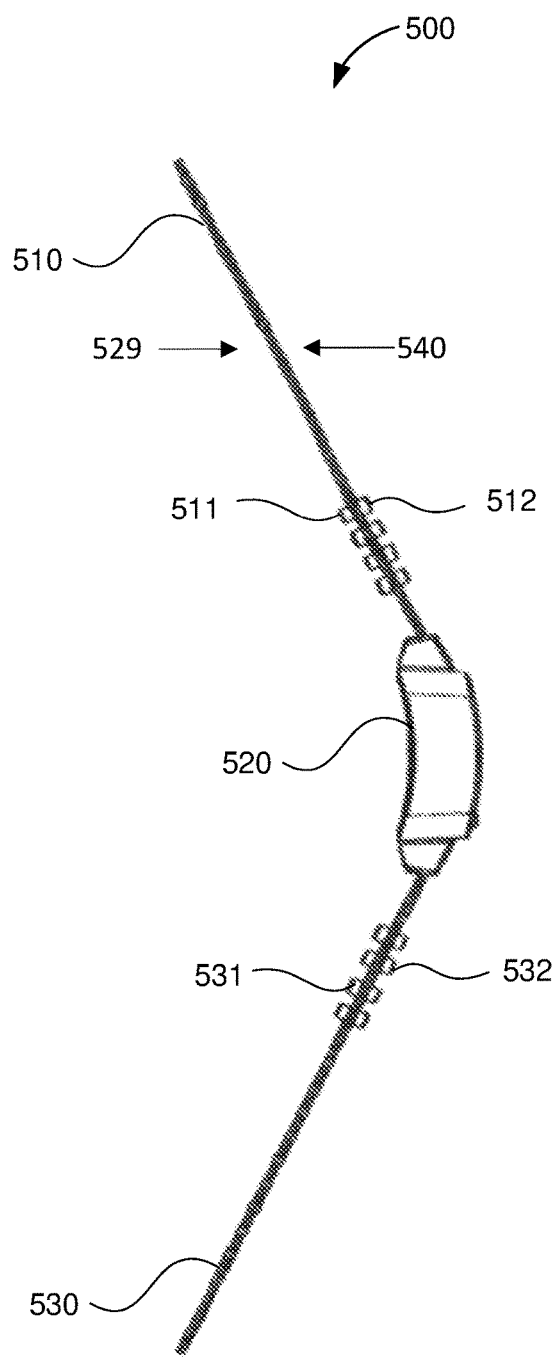

FIG. 5A shows a left side view of an example of a wrist-worn apparatus.

Figure 5B:
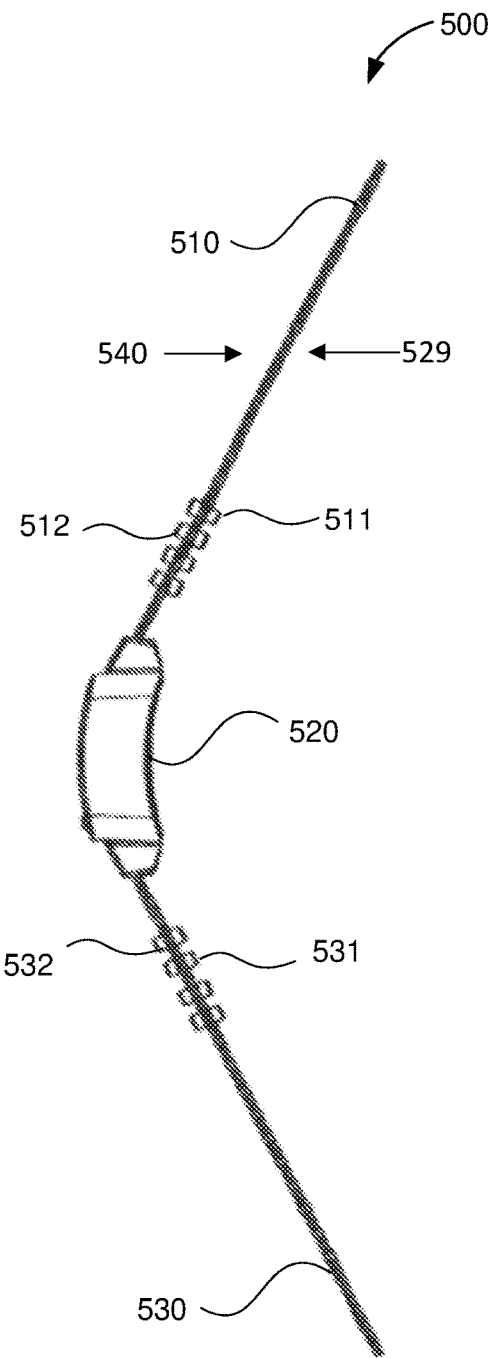

FIG. 5B shows a right side view of the wrist-worn apparatus of FIG. 5A.

Figure 6:
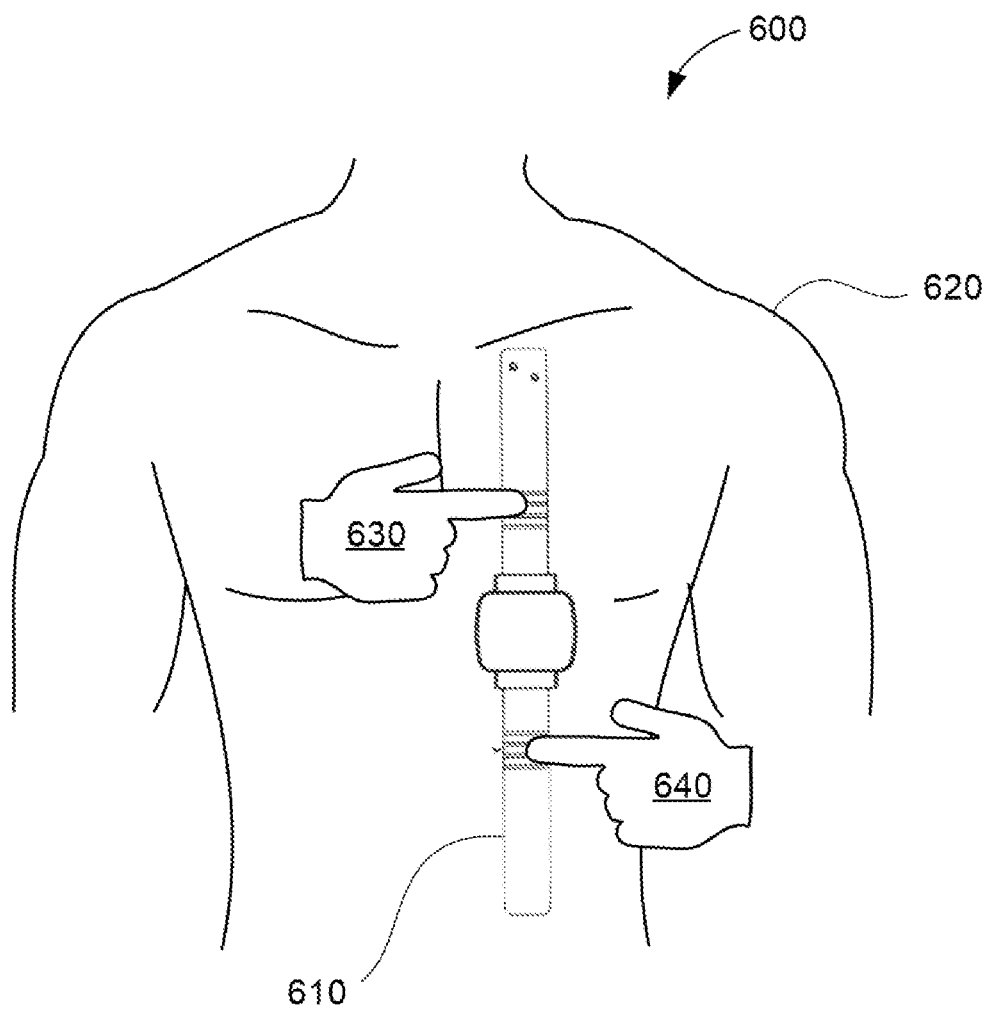

FIG. 6 shows a schematic diagram depicting placement of a wrist-worn apparatus.

Figure 7:
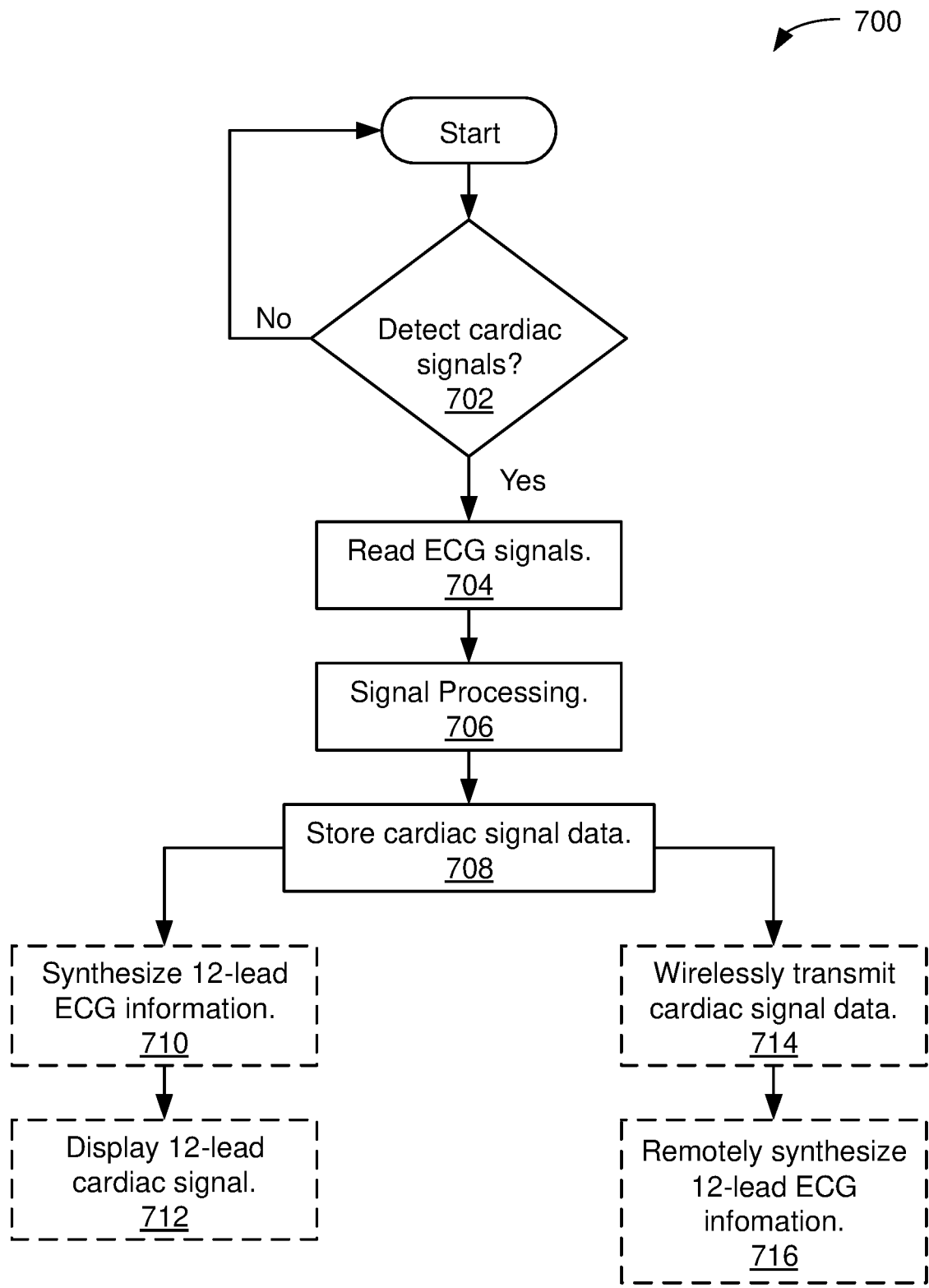

FIG. 7 shows a flowchart of an example operation for receiving and capturing cardiac signals using a wrist-worn apparatus as described herein.

Figure 8:
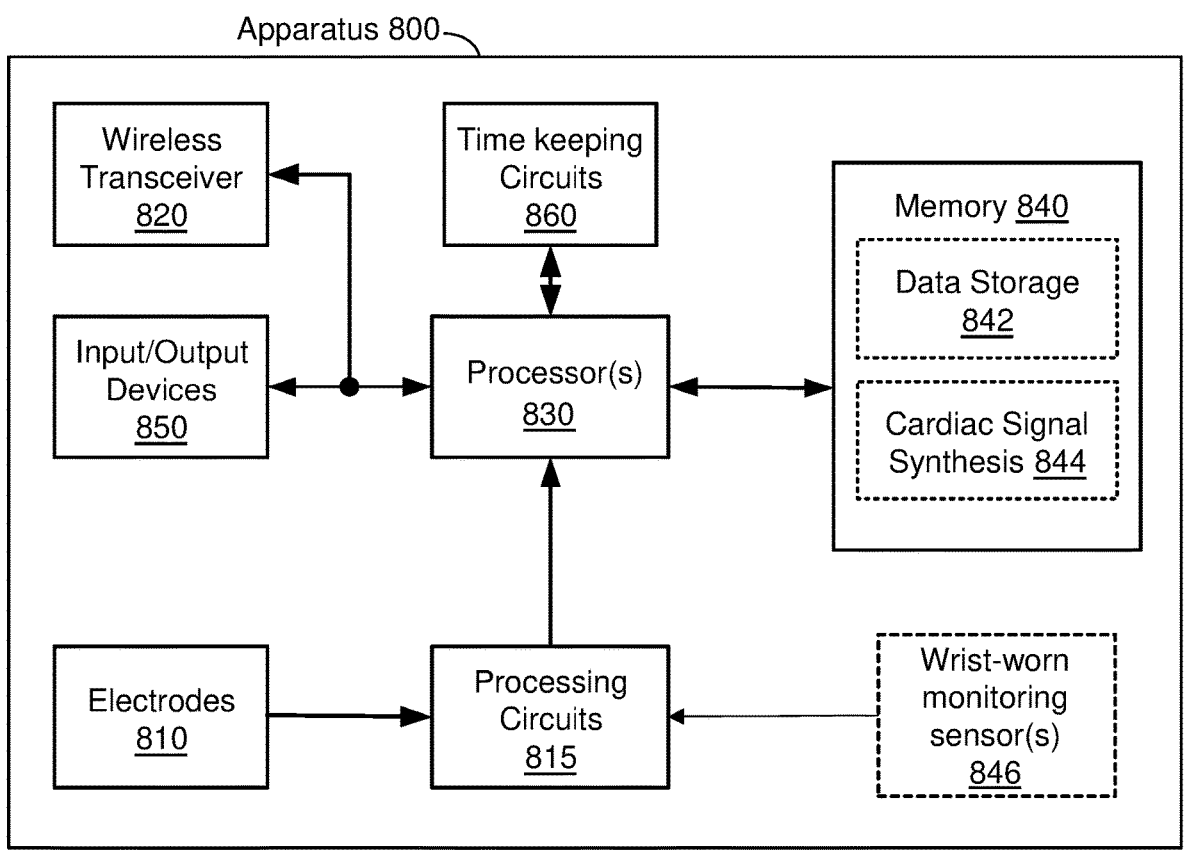

FIG. 8 shows a block diagram of a wrist-worn apparatus that may be included with any feasible wrist-worn apparatus described herein.

DETAILED DESCRIPTION

Described herein are apparatuses (including devices and systems) and methods for collection, observation, and/or monitoring of cardiac information. For example, described herein are apparatuses that are configured to be worn on a subject's wrist as a wristwatch, smartwatch, etc. in a first configuration and converted to a second configuration in which the apparatus is held by the subject against the subject's chest to capture and/or record three cardiac lead signals. These cardiac lead signals may be orthogonal and contain sufficient information to synthesize, derive, or determine conventional 12-lead cardiac data. These handheld devices may also perform one or more auxiliary functions, such as a timekeeping or watch function. By performing an auxiliary function, a patient may easily wear or carry the cardiac monitoring device, thereby enabling cardiac monitoring at a variety of locations, many beyond clinical settings.

In some examples, cardiac data associated with the three cardiac lead signals may be transmitted to a separate device for monitoring or analysis. For example, the three lead cardiac data may be transmitted to a remote unit (server, processor, computer, tablet computer, or the like) for processing, synthesis (to conventional 12-lead data), and/or display to a clinician. In other examples, the handheld device may include a processor that can perform the processing and synthesis and include a display to provide information to a user.

Figure 1A:
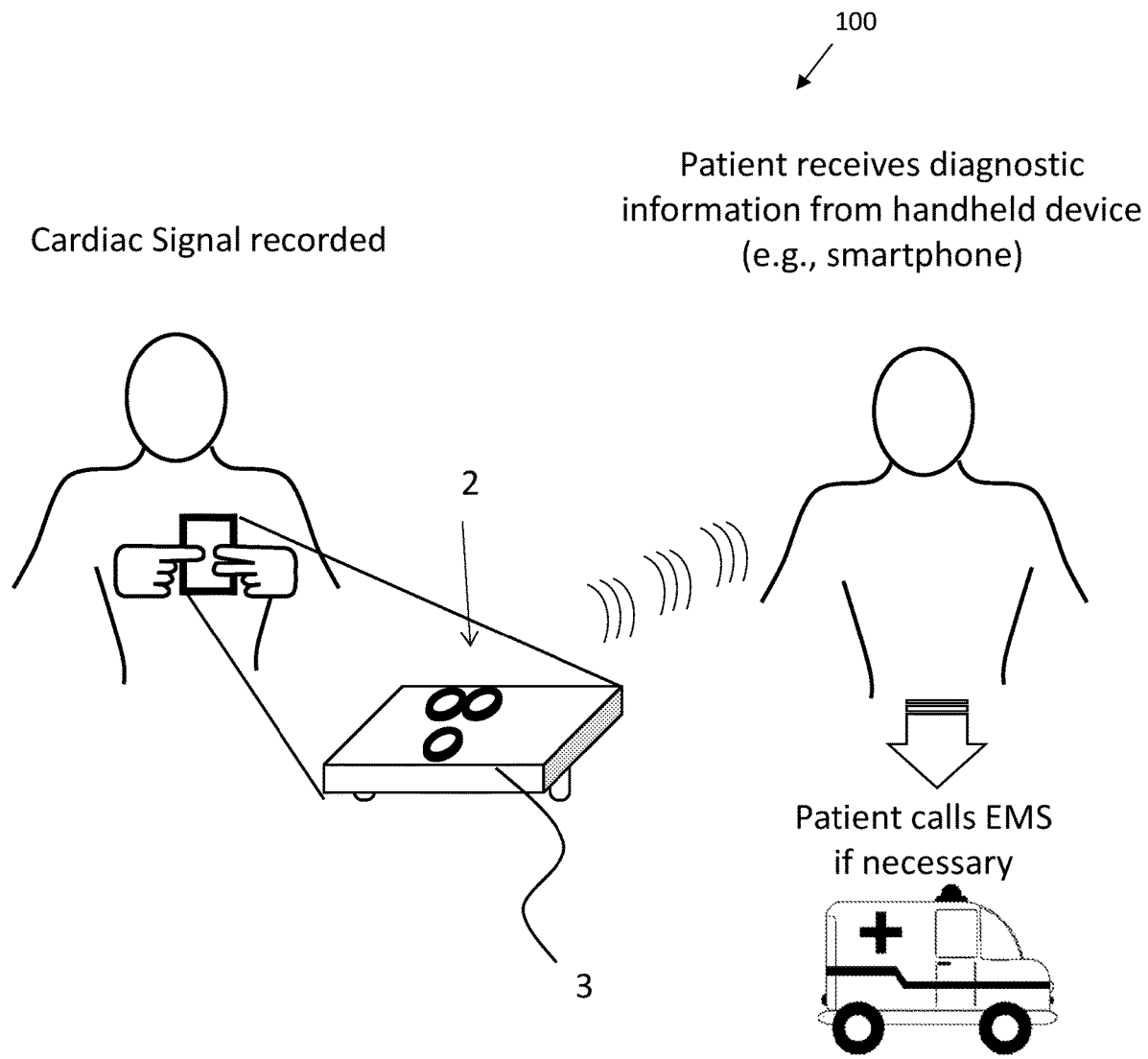
FIG. 1A illustrates one example of a system for cardiac signal detection and/or diagnosis.

FIG. 1A illustrates one example of a system 100 for cardiac signal detection and/or diagnosis. The wrist-worn apparatuses described herein may perform any or all of the functions illustrated and described with respect to FIGS. 1A-1B, 2A-2D, and 3A-3B, but may be configured as described herein. The system 100 may include a device 2 that includes one or more electrodes mounted, disposed, or coupled to the device (e.g., a housing 3). In FIG. 1A, a user (e.g., subject, patient or clinician) may capture and/or record cardiac signals (in some cases capturing and recording at two or more different times), and the handheld device 2 may process three orthogonal cardiac leads to compare the different times (e.g., baseline vs. assay time). A processor (not shown) of the handheld device 2 may further determine if the resulting differential cardiac lead signals (differential with respect to the two or more times the cardiac signals are recorded or "captured") indicates that a possible cardiac problem is present and can alert the user. FIG. 1B shows a view of another example of the system 100 including the handheld device 2 incorporating built in electrodes for cardiac signal acquisition, mounted directly on a housing 3 of the handheld device 2 and a remote processor (e.g., a personal computer (PC)) 4 connected via a telecommunication link to the handheld device 2.

The device 2 may further incorporate cardiac signal recording circuitry including one or more amplifiers, analog to digital converters (ADCs) for amplifying the cardiac signals detected by the electrodes, and data storage (e.g., memory) for storing cardiac signal data. The device 2 may also include communication circuitry operating on GSM, WWAN, Wi-Fi or any other feasible telecommunication standard for communication with a remote processor 4. In this manner, the device 2 may transmit recorded or captured cardiac signals or cardiac lead information to one or more remote devices such as the remote processor 4. The device 2 may include visual and/or audio circuits or devices (e.g., display, monitor, speaker, etc.) for communicating diagnostic information to the user.

The device 2 may communicate with the remote processor 4 via integrated communication circuitry. The remote processor 4 may, in turn, communicate with the handheld device 2 via an integrated communication module. The remote processor 4 may be equipped with diagnostic software for processing the received cardiac signals, producing diagnostic information and for transmitting the diagnostic information back to the device 2 for communicating the diagnostic information to the user via a speaker producing characteristic sounds or voice messages or in the form of graphical information via the visual and/or audio circuits or devices included with the device 2. As a consequence, the system 100 may be capable of performing automated detection of a cardiac condition on the basis of a 3-lead system and may not require interpretation of the diagnostic information by a specialist. Alternatively, instead of the remote processor 4, the device 2 may include a microprocessor within the housing 3 for processing the captured or recorded cardiac lead signals and producing diagnostic information.

FIGS. 2A, 2B and 2C show front, back and axonometric views, respectively, of an example of a device 200. The device 200 may be an example of the device 2 of FIGS. 1A and 1B. FIG. 2A shows the front view of the device 200 in a recording position as held by a patient. The device 200 may include the housing 3, and electrodes C, D, and G disposed on a front surface 6. FIG. 2B shows the back view of the device 200. As shown, electrodes A and B may be disposed on a back surface 5 of the housing 3. FIG. 2C shows the axonometric view of the device 200. This view shows the electrodes C, D, and G disposed on the front surface 6 of the housing 3 and electrodes A and B disposed on the back surface 5 of the housing 3. In some examples, the G electrode may be referred to as a ground electrode. The device 200 may also include additional electrodes to contact the patient hidden in this view.

The housing 3 of the handheld device 200 may incorporate the electrodes A, B, C, D, and G arranged in such an arrangement that enables recording of three electrocardiogram (ECG) lead signals. For example, the electrodes A and B mounted on the back surface 5 of the device may make contact with the chest of the patient in when the device 200 is in a recording position. The electrodes, A and B (which may be referred to as chest electrodes), are preferably arranged to cover a distance (e.g., be separated by) greater than at least 5 centimeters (cm), and preferably greater than about 10 cm. One reason for having such a spatial arrangement is to achieve a distance greater than an approximate diameter of the heart muscle which is needed to provide and/or improve possible lead orthogonality.

In addition to the two chest electrodes A and B, the handheld device in this example may include two other electrodes C and D, mounted on the front surface 6 substantially parallel and opposite to the back surface 5. These electrodes, C and D, may be used to capture or record cardiac signals from the patient's hands by pressing with fingers of the left and right hands respectively. The fifth electrode G may serve as a grounding electrode and is mounted on the front surface 6 for pressing with a left-hand finger.

Referring back to FIG. 2A, there is shown a view of one example of the device in a recording position. For operation, the patient may place his left hand so that patient's index and middle finger contact electrodes C and G respectively. Further, the patient may position and press the handheld device 200 against his chest so that the chest electrodes A and B contact his chest in the manner shown in FIG. 2D for producing tight contact between chest and the device. This may produce enough pressure for holding the device against the chest. Simultaneously, a finger of the right hand (or any other part of the right hand) may press the electrode D mounted on the front surface 6 of the housing 3.

Referring back to FIG. 2D, there is shown a front view of the device 200 placed against the patient's body in a recording position according to one example of the invention. In an optimal recording position, the center of the device 200 may be placed closely above the center of the heart so that the chest electrodes A and B are approximately on the midclavicular line (the vertical line passing through the midpoint of the clavicle bone), and the lower chest electrode B is at about the level of the lower end of the sternum.

The example in FIG. 3A shows a simple electrical scheme for obtaining a central point (CP) signal by connecting the electrodes of both hands via a simple resistive network consisting of two resistors. Similarly, FIG. 3B shows an electrical scheme for obtaining the CP signal using buffering and averaging via operational amplifiers. The CP signal may be used to provide an arbitrary reference (e.g., a reference voltage) that may be used in conjunction with signals from the electrodes A, B, C, D, E, and G to generate three orthogonal cardiac lead signals. In some examples, the three orthogonal cardiac lead signals may be used to generate a conventional 12-lead ECG signals. One method to transform the three orthogonal cardiac signals is described at least in U.S. patent application Ser. No. 17/494,806 and incorporated by reference herein.

As described herein, the apparatus (e.g., device, system, etc.) 200 may be implemented as a watch. Thus, the watch may be worn by the subject and may be used whenever convenient to capture, record, and/or transmit cardiac signals or data. In this manner, the apparatus 200 may be a wearable cardiac diagnosis device. One such implementation is described with respect to FIGS. 4-6.

In general, the use of a resistive network is optional. Any of the apparatuses described herein may be used without a resistive network or may not include a resistive network as describe. For example, the apparatus may be configured to record two (or more) channels, and store and/or transmit the recorded channels for direct analysis by a physician and/or software, or for further processing.

FIG. 4A shows a front view of a wrist-worn apparatus 400. As depicted in FIG. 4, the wrist-worn apparatus 400 may be implemented as a wrist-worn watch. The wrist-worn apparatus 400 may include a first wrist band portion 410, a housing 420, and a second wrist band portion 430. The first wrist band portion 410 may be removably coupled to the second wrist band portion 430 by a clasp, latch, etc., thereby enabling the patient to wear the wrist-worn apparatus 400 on the subject's wrist. The wrist-worn apparatus may be configured to be slightly biased (as shown in FIGS. 5A-5B) in the wrist-worn configuration or may be relatively flat in the linear (unlatched) configuration. The biased, slightly concave configuration shown in FIGS. 5A-5B may help maintain contact with the apparatus against the patient's chest.

The housing 420 may include a display 421 that may be used to provide information to the patient. For example, when operating in a first mode, the display 421 may provide conventional watch related information such as time of day, date, and other chronometer information. In some examples the apparatus may be configured to provide instructions on using the wrist-worn apparatus to record ECG signals. For example the wrist-worn apparatus may be configured to operate in a second mode to record ECG signals, and the display 421 may provide information related to ECG information, including instructions on how to position and use the apparatus to record ECG information. For example, the display 421 may show images regarding the placement of the wrist-worn apparatus 400 on the patient's body. In another example, the display 421 may show usage instructions and/or information regarding the capture and analysis of a patient's cardiac lead signals. In some examples, the housing 420 may enclose a speaker (not shown) that may provide acoustic information to the patient. For example, the speaker may provide audible directions regarding the usage or placement of the wrist-worn apparatus 400. In another example, the speaker may provide tones associated with capturing cardiac lead signals.

In some examples, the housing 420 may enclose a transceiver 422 that may be configured to communicate with any other feasible device. For example, the housing 420 may enclose a Bluetooth transceiver that may be used to communicate cardiac signal data with any feasible Bluetooth enabled device, such as a smart phone, or the like. In another example, the housing 420 may enclose a Wi-Fi transceiver that may be used to communicate cardiac signal data with any feasible Wi-Fi enable device including computers (laptop computers, desktop computers, tablet computers, or the like), Wi-Fi access points, smart phones, etc. In still another example, the housing 420 may enclose a cellular transceiver that may be used to communicate cardiac signal information via any feasible cellular network.

In some examples, the cardiac data (e.g., captured cardiac lead signals) may be analyzed on a remote processor (such as the remote processor 4 of FIG. 1B). For example, the cardiac data may directly or indirectly be transmitted to the remote processor 4 using the transceiver 422 included within the housing 420. In some other examples, the housing 420 may enclose a processor 423. The processor 423 may analyze any captured and/or recorded cardiac lead signals. For example, any operations that may be performed by the remote processor 4 may be performed by the processor 423. In any of the apparatuses described herein the circuitry and/or processor may be integrated into the strap(s), rather than, or in addition to, a housing.

The first wrist band region 410 may include a first electrode 411 and a second electrode disposed (shown in FIG. 4B) on the inside surface of the first wrist band portion 410 and the second wrist band portion 430. The inside surface may refer to the surface configured to be worn against the wrist when in the first, wrist-worn configuration, which may also be configured to be held against the chest in the ECG collection configuration. The second electrode may be on the second wrist band region 430 or it may be on the housing 420 (not shown). The third electrode 431 and a fourth electrode 432 may be disposed on the opposite side of the apparatus, such as the opposite (outward-facing) sides of the first wrist band region 410 and the second wrist-band region, and/or on the housing. In some examples, portions of the patient's body may contact the first electrode 411 and the second electrode 431 in order for the processor 423 to determine three orthogonal cardiac lead signals. For example, a right finger may be placed in contact with the third electrode 412 and a left finger may be placed in contact with the fourth electrode 432.

FIG. 4B shows a rear view of the wrist-worn apparatus 400. As mentioned, the third electrode 412 may be disposed on the first wrist band region 410 opposite the first electrode 411. Similarly, the fourth electrode 432 may be disposed on the second wrist band region 430 opposite the third electrode 431. In some uses, the wrist-worn apparatus 400 may be placed on the chest of the patient thereby placing the second electrode 412 and the fourth electrode 432 in contact with the chest. In some examples, first electrode 411 may be separated from the second electrode 431 by a distance of at least 5 centimeters (cm). In some cases, the separation distance may be at least 10 cm so that the second electrode 412 and the fourth electrode 432 may span a distance larger than a typical heart muscle. Thus, the first electrode 411 and the second electrode 431 may receive electrical signals from the patient's heart.

The patient may be guided by the wrist-worn apparatus 400 to correctly place the wrist-worn apparatus 400 on an optimal position on the chest so that the first electrode 411 and the second electrode 431 may capture and/or detect cardiac signals from the patient's heart. For example, the wrist-worn apparatus 400 may provide one or more images on the display 421 and/or provide audible instructions through a speaker 425 to guide placement of the wrist-worn apparatus 400 on the patient. In some examples, a back of the housing 420 may act as an additional or alternative electrode. For example, the back of the housing 420 may perform the functions associated with a ground electrode.

The housing 420 may enclose circuitry 424 to capture and/or record cardiac lead signals from one or more of the first, second, third, and fourth electrodes 411, 431, 412, and 432 respectively. In some examples, the circuitry 424 may capture and/or record cardiac lead signals from a ground electrode (such as the back of the housing 420, or any of the described electrodes performing the function of the ground electrode. Thus, the first electrode 411, the second electrode 431, the third electrode 412, and the fourth electrode 432 (and in some cases the housing 420) may be coupled to circuitry 424 to capture and/or record cardiac lead signals. In some examples, the circuitry 424 may include any number of feasible filters, amplifiers, analog-to-digital converters, memory, and the like to capture and/or record cardiac signals.

In some examples, the processor 423, in conjunction with the circuitry 424, may receive data from one or more coupled electrode and determine one or more sets of orthogonal three-lead cardiac signals. In some examples, the processor 423 can record sensor data from one or more electrodes, three-lead cardiac data, or synthesized (e.g., derived) 12-lead cardiac data (e.g., 12-lead electrocardiogram (ECG) information). The processor 423 in conjunction with the transceiver 422 may transmit cardiac data (including orthogonal three-lead cardiac signal data) to another device for further processing or analysis. In some examples, the processor 423 or a separate device may process captured or recorded cardiac data to synthesize conventional 12-lead cardiac data. That is, the three-lead cardiac signal data may include all the information sufficient to synthesize conventional 12-lead cardiac data.

In some examples, the processor 423 can process cardiac signal data collected through electrodes and the circuitry 424 and determine that placement of the wrist-worn apparatus 400 is incorrect. The processor 423 may also instruct the user to correct placement of the wrist-worn apparatus 400 and/or correct placement of fingers on any feasible electrode. For example, the processor 423 can provide the instructions to the user through the speaker 425 and/or a display.

FIG. 5A shows a left side view of a wrist-worn apparatus 500. The wrist-worn apparatus 500 may include a first wrist band region 510, a housing 520, and a second wrist band region 530. The wrist-worn apparatus 500 may be an example of the wrist-worn apparatus 400 of FIGS. 4A and 4B. Thus, the first wrist band region 510 may be an example of the first wrist band 410, the housing 520 may be an example of the housing 420, and the second wrist band region 530 may be an example of the second wrist band 430.

As shown, the first wrist band region 510 may include a first electrode 511 and a third electrode 512. The second wrist band region 530 may include a second electrode 531 and a fourth electrode 532. FIG. 5B shows a right side view of the wrist-worn apparatus 500. The wrist-worn apparatus 500 includes the first wrist band region 510, the housing 520, and the second wrist band region 530. In some examples, the back of the housing 520 may perform as a fifth electrode.

The first, second, third, and fourth electrodes 511, 531, 512, and 532 may be electrically coupled to circuits or the like within the housing 520 by one or more conductors (wires, or the like) included with, or embedded within the first wrist band 510 and the second wrist band 530.

In some examples, the wrist-worn apparatus 500 may operate in a first mode as a watch or any other similar or feasible time keeping device (e.g., a chronometer). In some cases, the first wrist band region 510 may be removably coupled to the second wrist band region 530 to form a continuous loop with the housing 520. When so coupled, the wrist-worn apparatus 500 may be easily and comfortably worn on a user's or patient's wrist. Although the strap ("wrist band") shown in FIGS. 4A-4B and 5A-5B includes two parts, each connected to the housing, in some examples a single strap or band is included and may be coupled to a housing or the housing may be integrated into the strop or band. In examples having a single strap or band, the apparatus may include a first region and a second region that are both on the same band or strap.

The wrist-worn apparatus 500 may operate in a second mode to capture one or more cardiac signals through one or more electrodes. In the second mode, the wrist bands may be uncoupled from each other and the wrist-worn apparatus may be placed on the patient's chest. In this manner, the second electrode 531 and the first electrode 511 (and optionally the housing 520) may be placed in contact with the chest of the patient. In some examples, the second electrode 531 may be separated from the first electrode 511 by a distance of at least 5 cm and in some cases by a distance of at least 10 cm (e.g., between 5 cm and 14 cm, between 6 cm and 12 cm, between 8 cm and 12 cm, etc.), particularly when the wrist-worn apparatus 500 is placed on the patient's chest.

In the second mode, a processor (included within the housing 520) may capture, record, and in some cases analyze the cardiac signals. For example, the processor may synthesize conventional 12-lead ECG information from cardiac signals received by one or more electrodes of the wrist-worn apparatus 500. Alternatively, or additionally, the wrist-worn apparatus 500 can transmit data associated with the captured cardiac signals to another device thereby enabling remote monitoring and/or analysis of the patient's cardiac health. In some examples, the device receiving the data may synthesize the conventional 12-lead ECG information.

FIG. 5B shows a right side view of the wrist-worn apparatus 500. The wrist-worn apparatus 500 includes the first wrist band region 510, the housing 520, and the second wrist band region 530. The first wrist band region 510 includes the first electrode 511 and the second electrode 512. In this example, the second wrist band region 530 includes the second electrode 531 and the fourth electrode 532. In FIGS. 4A-4B and 5A-5B multiple adjacent electrodes are shown on the inner surface 529 and outer surface 540, though in some examples on single electrodes are used. Alternatively or additionally, multiple electrodes may be used and the overall system may be filtered FIG. 6 shows a schematic diagram 600 depicting placement of a wrist-worn apparatus 610 as described in FIGS. 4A-4B and 5A-5B. The wrist-worn apparatus 610 may be placed on (over) the patient's 620 left chest such that the electrodes contacting the chest are approximately straddling the patient's heart. Fingers from the patient's hands may be placed in contact with electrodes. For example, a finger from the patient's left hand 630 may be placed in contact with one electrode on a wrist band and another finger from the patient's right hand 640 may be placed in contact with another electrode on a different wrist band.

In some examples, the wrist-worn apparatus 610 may guide the patient in optimizing the placement of the wrist-worn apparatus on the patient 620. For example, a processor within the wrist-worn apparatus 610 may receive one or more cardiac signals, particularly from electrodes in contact with the patient's chest. The wrist-worn apparatus 610 may analyze these signals and determine that the placement of the wrist-worn apparatus 610 is incorrect. In response, the wrist-worn apparatus 610 may display placement instructions or, in some cases, may provide audible instructions to guide the patient to correct the placement of the wrist-worn apparatus 610.

The form of the apparatus shown in FIGS. 4A-4B, 5A-5B and 6 is just one example of a wrist-worn apparatus. In some examples the wrist-worn apparatus does not include a watch body having a watch face but is a single continuous strap. The strap may include the first portion and second portion as described herein. In some examples a body may be included but may not be configured as a watch body.

FIG. 7 shows a flowchart 700 of an example operation for receiving and capturing cardiac signals using a wrist-worn apparatus. The wrist-worn apparatus may be the wrist-worn apparatus 400 of FIGS. 4A and 4B, the wrist-worn apparatus 500 of FIGS. 5A and 5B, the wrist-worn apparatus 610 of FIG. 6, or any other feasible wrist-worn apparatus. In FIG. 7, the operation begins as wrist-worn apparatus detects cardiac signals in block 702. For example, the wrist-worn apparatus may detect cardiac signals for a set of three-lead cardiac signals through included electrodes. The cardiac signals may be detected through one or more electrodes. If no cardiac signals are detected, then the operation may continue to periodically (or continuously) check to see if any cardiac signals are detected. On the other hand, if cardiac signals are detected, then in block 704, the wrist-worn apparatus may read and/or process the ECG (cardiac) signals. In some examples, the detection of cardiac signals may cause the wrist-worn apparatus to transition from a first mode (e.g., a time keeping mode operating as a watch, for example) to a second mode to capture cardiac signals. Alternatively or additionally the user may select a control or input to indicate that the mode is switching from timekeeping, etc., to detecting an ECG signal. By waiting until cardiac signals are detected, the wrist-worn apparatus may save power by operating in a low-power watch mode instead of a relatively higher power mode to capture and/or process cardiac signals.

In block 704, the wrist-worn apparatus can read (capture) ECG (cardiac) signals. For example, the wrist-worn apparatus can capture cardiac signals through one or more included electrodes. Next, in block 706 the wrist-worn apparatus can provide signal processing to the captured cardiac signals. For example, the cardiac signals may be buffered, amplified, digitized (through one or more analog-to-digital converters, for example), or the like. In block 708, the processed cardiac signals may be stored in a memory.

Next, in block 710, a 12-lead ECG information may be synthesized from the processed cardiac signal data. This operation may be optional, as denoted by dashed lines in FIG. 7. Thus, the wrist-worn apparatus may include a processor that may synthesize (derive, determine) 12-lead ECG information from processed cardiac signal data, including processed cardiac signal data that may include three-lead cardiac signal data. In block 712, the wrist-worn apparatus may display 12-lead ECG information data on a display. In some examples, the display may be separate from the wrist-worn apparatus.

Returning to block 708, the wrist-worn apparatus may wirelessly transmit the processed cardiac signal data in block 714. For example, the wrist-worn apparatus may transmit captured three-lead cardiac signal data directly or indirectly to one or more remote devices. In block 716, the remote devices can synthesize a 12-lead ECG information. The 12-lead ECG information may be analyzed or monitored by a clinician to ascertain the cardiac health of the patient.

FIG. 8 shows a block diagram of an example wrist-worn apparatus 800. The wrist-worn apparatus 800 may include electrodes 810, processing circuits 815, a wireless transceiver 820, a processor 330, a memory 840, input/output devices 850, and time keeping circuits 860.

The electrodes 810 may be included within the wrist-worn apparatus 800, or external to the wrist-worn apparatus 800, such as disposed on one or more wrist bands (not shown). The electrodes 810 may be coupled to processing circuits 815. The processing circuits may include buffers, amplifiers, analog-to-digital converters, or the like to capture and/or digitize cardiac signals received by the electrodes 810. The processing circuits 815 may be coupled to the processor 830.

The wireless transceiver 820, which may include circuits and/or device to provide wireless communications with any other feasible device, is coupled to the processor 830. In some examples, the wireless transceiver 820 may include Bluetooth, Wi-Fi, cellular, or any other feasible wireless communication circuits. In some examples, the processor 830 may transmit captured cardiac signal data through the wireless transceiver 820 to other devices that may, in turn, synthesize conventional 12-lead ECG information data therefrom.

The input/output devices 850, which is coupled to the processor 830, may include visual and/or audio devices to display or provide audible feedback or information to a patient or clinician. The time keeping circuits 860, which are also coupled to the processor 830, may be used to provide time of day information that may be displayed on a display, such as one included within the input/output devices 850.

The processor 830, which is also coupled to the memory 840, may be any one or more suitable processors capable of executing scripts or instructions of one or more software programs stored in the wrist-worn apparatus 800 (such as within memory 840).

The memory 840 may include a data storage region 842 that may be used to locally store cardiac signal data collected from the electrodes 810. For example, the electrodes 810 may receive cardiac signals that are processed by the processing circuits 815 and then stored in the data storage region 842.

The memory 840 may also include a non-transitory computer-readable storage medium (e.g., one or more nonvolatile memory elements, such as EPROM, EEPROM, Flash memory, a hard drive, etc.) that may store the following software modules: a Cardiac signal synthesis module 844 to synthesize 12-lead ECG information. Each software module includes program instructions that, when executed by the processor 830, may cause the wrist-worn apparatus 800 to perform the corresponding function(s). Thus, the non-transitory computer-readable storage medium of memory 840 may include instructions for performing all or a portion of the operations described herein.

The processor 830 may execute the cardiac signal synthesis module 844 to generate or synthesize conventional 12-lead ECG information from cardiac signal data that may be stored in the data storage region 842. For example, orthogonal 3-lead cardiac signal data may be captured through the electrodes 810 and then stored in the data storage region 842. Execution of the cardiac signal synthesis module 844 may cause the processor 830 to retrieve some or all of the cardiac signal data stored in the data storage region 842 and generate 12-lead ECG information based thereon. One method to transform the three orthogonal cardiac signals into 12-lead ECG information is described at least in U.S. patent application Ser. No. 17/494,806 and incorporated by reference herein.

Optionally, any of these apparatuses may include sensing for cardiac events when the device is worn on the wrist, in order to trigger an alert to the user or a caregiver (e.g., doctor, nurse, technician, family member, etc.) to use the device to take readings as described above. For example, as shown in FIG. 8, any of these apparatuses may include wrist-worn monitoring using one or more sensors. In some examples the sensors may be the electrode(s) 810 used for measuring from the chest, while in other apparatus examples separate, dedicated sensors 846 may be used. For example, one or more Photoplethysmography (PPG) sensors on the apparatus, such as on the strap and/or housing may be used. The processing circuits 815 may be configured to process signals when the device is worn on the wrist of the patient and may periodically or continuously monitor the patient based on the signal(s) sensed. In some examples the signals may be detected from sensors on different portions of the inner surface of the strap and/or housing (e.g., watch housing) to determine which sensor(s) are detecting the presence of the patient and a cardiac signal. For example, if PPG is used, the PPG signal may detect the heartbeat and the regularity of the heartbeat may be determined.

With either electrical (e.g., electrodes) or PPG signals, a time-domain analysis of the signal(s) may be done to extract features that may indicate cardiac problems. The apparatus may use extracted features to determine if the patient is in or is likely to be in, cardiac distress. Determination of diseased vs. healthy states may be performed by the processing circuits 815 and/or processor 830, based on e.g., decision trees, discriminant analysis, logistic regression, etc.

In some examples the apparatus may provide continuous (or periodic) monitoring and recording as described above and may denoise the signal and/or may preprocess (e.g., filter) the signal or use the raw signal to determine heart rate variability (HRV). If the HRV exceed a threshold, which may be adjusted for the patient specifically or may be generic, the apparatus may trigger the alert.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A wrist-worn apparatus configured to measure ECG signals, the apparatus comprising:
   a first wrist band portion including a first electrode and a second electrode;
   a second wrist band portion including a third electrode and a fourth electrode; and
   a processor configured to process three orthogonal cardiac leads derived from the first, second, third and fourth electrodes,
   wherein the apparatus is configured to operate in a first mode to be worn on a subject's wrist when the first wrist band portion is coupled to the second wrist band portion to form a continuous loop worn on a subject's wrist and is further configured to operate in a second mode to capture bioelectric signals wherein the first electrode and the third electrode are on an inner side of the apparatus and are configured to contact the subject's chest, and the second electrode and the fourth electrode are on an outer side of the apparatus, configured to be held by two of the subject's fingers when the first wrist band portion is uncoupled from the second wrist band portion and the wrist band portions are placed on the subject's chest and held by the two of the subject's fingers.

2. The apparatus of claim 1, wherein the first electrode and the third electrode are configured to contact the subject's chest when the apparatus is operating in the second mode.

3. The apparatus of claim 1, further comprising a display configured to display a time of day when the apparatus is operating in the first mode.

4. The apparatus of claim 3, wherein the display is configured to show an orientation of the apparatus on the subject's chest when the apparatus is operating in the second mode.

5. The apparatus of claim 1, wherein the second electrode is configured to be placed in contact with a finger from the subject's first hand and the fourth electrode is configured to be place in contact with a finger from the subject's second hand, the subject's second hand being different than the subject's first hand, when the apparatus is operating in the second mode.

6. The apparatus of claim 1, wherein the first electrode is on an inner surface of the first wrist band portion and the third electrode is on an inner surface of the second wrist band portion.

7. The apparatus of claim 1, wherein the second electrode is on an outer surface of the first wrist band portion and the fourth electrode is on an outer surface of the second wrist band portion.

8. The apparatus of claim 1, wherein the apparatus is configured to receive bioelectric signals from the subject's chest when operating in the second mode.

9. The apparatus of claim 1, wherein the apparatus is configured to receive bioelectric signals from the subject's fingers when operating in the second mode.

10. The apparatus of claim 1, further comprising a resistive network forming a central point in a sagittal plane through the subject's chest passing between the third and fourth electrodes when the first wrist band portion and the second wrist band portion are held against the subject's chest, wherein the three orthogonal cardiac leads are formed from the first, second, third and fourth electrodes and the central point.

11. The apparatus of claim 1, wherein the processor is configured to record and transmit the three orthogonal cardiac leads.

12. The apparatus of claim 1, wherein the processor is configured to synthesize conventional 12-lead electrocardiogram (ECG) information from the three orthogonal leads.

13. A wrist-worn apparatus configured to measure ECG signals, the apparatus comprising:
a first wrist band portion including a first electrode and a second electrode;
a second wrist band portion including a third electrode and a fourth electrode; and
a processor configured to process three orthogonal cardiac leads derived from the first, second, third and fourth electrodes,
wherein the apparatus is configured to operate in a first mode to be worn on a subject's wrist and display time when the first wrist band portion is coupled to the second wrist band portion to form a continuous loop worn on a subject's wrist and is further configured to operate in a second mode to capture bioelectric signals from the subject wherein the first electrode and the third electrode are on an inner side of the apparatus and are configured to contact the subject's chest and the second electrode and the fourth electrode are on an outer side of the apparatus, configured to be held by two of the subject's fingers when the first wrist band portion is uncoupled from the second wrist band portion and the wrist band portions are placed on the subject's chest and held by the two of the subject's fingers.

14. A method of detecting a cardiac signal from a subject, the method comprising:

operating an apparatus in a first mode when a first wrist band portion of the apparatus is coupled to a second wrist band portion of the apparatus and worn on the subject's wrist;
operating the apparatus in a second mode when the first wrist band portion is uncoupled from the second wrist band portion, the operation in the second mode comprising:
placing the first wrist band portion and the second wrist band portion of the apparatus against the subject's chest so that a first electrode on an inner surface of the first wrist band portion is in contact with the subject's chest and a second electrode on an inner surface of the second wrist band portion is in contact with the subject's chest, wherein the first electrode is separated from the second electrode by a distance greater than a diameter of the subject's heart;
placing a finger of a first hand against a third electrode on an outer surface of the apparatus and a finger of a second hand against a fourth electrode of the apparatus to hold the apparatus against the subject's chest; and
measuring electrocardiogram (ECG) information from the first, second, third and fourth electrodes.

15. The method of claim 14, wherein measuring the ECG information comprises measuring three orthogonal leads using a resistive network forming a central point in a sagittal plane through the subject's chest passing between the third and fourth electrodes when the first wrist band portion and the second wrist band portion are held against the subject's chest, wherein three orthogonal cardiac leads are formed from the first, second, third and fourth electrodes and the central point.

16. The method of claim 15, further comprising: processing the three orthogonal cardiac leads to synthesize conventional 12-lead electrocardiogram (ECG) information; and outputting the conventional 12-lead ECG information.

17. The method of claim 15, wherein processing the three orthogonal cardiac leads comprises using a processor housed within a housing positioned between the first wrist band portion and the second wrist band portion.

18. The method of claim 15, wherein placing the finger of the first hand against the third electrode comprises placing the finger of the first hand against the third electrode on an outer surface of the first wrist band portion and placing the finger of the second hand against the fourth electrode comprises placing the finger of the second hand against the fourth electrode on an outer surface of the second wrist band portion.

19. The method of claim 14, wherein operation in the first mode comprises displaying time of day, date or a combination thereof on a display of the apparatus.

20. The method of claim 14, wherein operation in the second mode comprises displaying images regarding placement of the apparatus on the subject's chest on a display of the apparatus.

* * * * *